United States Patent [19]

Holick et al.

[11] Patent Number: 5,254,538
[45] Date of Patent: Oct. 19, 1993

[54] METHOD OF TREATING PERIODONTAL DISEASE

[75] Inventors: Michael F. Holick, Sudbury; Xiao Tian, Boston, both of Mass.

[73] Assignee: Trustees of Boston University, Boston, Mass.

[21] Appl. No.: 826,230

[22] Filed: Jan. 27, 1992

Related U.S. Application Data

[63] Continuation of Ser. No. 416,781, Oct. 4, 1989, abandoned.

[51] Int. Cl.$^5$ .................. A61K 31/70; A61K 31/59; A61K 7/16
[52] U.S. Cl. .................. 514/35; 514/167; 424/49
[58] Field of Search .................. 514/35, 167, 928; 424/49

[56] References Cited

U.S. PATENT DOCUMENTS

| | | | |
|---|---|---|---|
| 3,622,668 | 11/1971 | Moss | 424/237 |
| 3,655,881 | 4/1972 | Jackson et al. | 424/144 |
| 4,225,596 | 9/1980 | DeLuca et al. | 424/236 |
| 4,335,120 | 6/1982 | Holick et al. | 514/167 |
| 4,391,802 | 7/1983 | Suda et al. | 424/236 |
| 4,410,515 | 10/1983 | Holick et al. | 536/4.1 |
| 4,414,202 | 11/1983 | Silvetti | 424/147 |
| 4,521,410 | 6/1985 | Holick et al. | 514/26 |
| 4,588,716 | 5/1986 | DeLuca et al. | 514/168 |
| 4,610,978 | 9/1986 | Dikstein et al. | 514/167 |
| 4,634,692 | 1/1987 | Partridge et al. | 514/167 |
| 4,719,205 | 1/1988 | DeLuca et al. | 514/167 |
| 4,728,643 | 3/1988 | Holick et al. | 514/167 |
| 4,749,572 | 6/1988 | Ahari | 424/132 |
| 4,837,024 | 6/1989 | Michaeli | 424/446 |
| 4,844,898 | 7/1989 | Komori et al. | 424/150 |

FOREIGN PATENT DOCUMENTS

| | | |
|---|---|---|
| 0129003 | 12/1984 | European Pat. Off. |
| 0177920 | 4/1986 | European Pat. Off. |
| 2249414 | 4/1974 | Fed. Rep. of Germany |
| 3800972 | 7/1989 | Fed. Rep. of Germany |
| 55-111460 | 8/1980 | Japan |
| 57-149224 | 9/1982 | Japan |
| 58-216178 | 1/1983 | Japan |
| 84/02845 | 8/1984 | PCT Int'l Appl. |
| 89/03873 | 5/1989 | PCT Int'l Appl. |

OTHER PUBLICATIONS

Saitoh, T., Effect of 1α-hydroxycholecalciferol and anabolic steroids on the healing of experimental extraction wounds, studied by microradiogram and calcium-45 autoradiogram, *Chem. Abstr.* 96:194070y (1982).

Tian et al. 1,25-Dihydroxyvitamin D$_3$: A Novel Agent For Wound Healing, *Clinical Res.* 38:640A (1990).

Greenspan and Goldhaber, "Oral Manifestations of Disease", in *Harrison's Principles of Internal Medicine*, 12th ed., Wilson et al., eds., McGraw-Hill, Inc., New York, pp. 242-243 (1991).

McGuigan, J., "Peptic Ulcer and Gastritris", in *Harrison's Principles of Internal Medicine*, 12th ed., Wilson et al., McGraw-Hill, Inc., New York, pp. 1229-1239 (1991).

Abe, J. et al., *Proc. 7th Workshop on Vitamin D*, pp. 310-319 (1988).

Clemens, T. L. et al., *J. Clin. Endo. and Metab.* 56:824-830 (1983).

Danon, D. et al., *Proc. Natl. Acad. Sci. USA* 86:2018-2020 (1989).

(List continued on next page.)

*Primary Examiner*—Frederick E. Waddell
*Assistant Examiner*—Kimberly R. Jordan
*Attorney, Agent, or Firm*—Sterne, Kessler, Goldstein & Fox

[57] ABSTRACT

The invention relates to methods for enhancing wound healing; enhancing gastric, duodenal, esophageal, decubitus, genito urinary ulcer and ulcerative keratitis healing; inhibiting scar formation; and treating periodontal disease in an animal by the topical, oral parenteral, transdermal or ophthalmic administration of a vitamin D compound.

8 Claims, 2 Drawing Sheets

OTHER PUBLICATIONS

Franceschi, R. T. et al., *J. Biol. Chem.* 262:4165–4171 (1987).

Holick, M. F. et al., *New Eng. J. Med.* 303:349–354 (1980).

Hung, V. C. et al., *Arch. Dermatol.* 125:65–69 (1989).

Lynch, S. E. et al., *J. Clin. Invest.* 84:640–646 (1989).

Shiina, Y. et al., *Arch. Biochem. and Biophys.* 220:90–94 (1983).

Van Bokhoven, M. G. J. et al., *Brit. J. Dermatol.* 119:737–742 (1988).

MacLaughlin, J. et al., 9th Int'l. Congress on Photobiology and 12th Ann. Mtg. Amer. Soc. Photobiol., 1984 Abstract MAM-D5.

Hosomi, J. et al., *Endocrinology* 3:1950–1957 (1983).

Honma, Y. et al., *Proc. Natl. Acad. Sci (USA)* 80:201–204 (1983).

Holick, M., "The Photobiol. of Vitamin $D_3$ in Man," pp. 197–216 (1984).

Morimoto, S., *Chem. Abstr.* 106:23300u (1986).

METHOD OF TREATING PERIODONTAL DISEASE

This application is a continuation of application Ser. No. 07/416,781, filed Oct. 4, 1989 now abandoned.

FIELD OF THE INVENTION

The invention is in the field of medicinal chemistry. In particular, the present invention relates to novel methods for accelerating wound and ulcer healing and for treating periodontal disease using vitamin D-related compounds.

BRIEF DESCRIPTION OF THE BACKGROUND ART

Human skin is a complex integration of different types of cells and tissues which form an organ. Skin is also the primary seat of the sense of touch and creates a covering for the protection of the deeper tissues. The skin also plays an important role in the regulation of body temperature and is also an excretory and absorbing organ. Skin consists primarily of a layer of vascular tissue and an external covering of epithelium known as the epidermis. On the surface layer are the sensitive papillae and alongside or imbedded beneath it are certain specialized organs, specifically the sweat glands, hair follicles, and sebaceous glands.

In order to defend the tissues below from trauma, the skin must be tough, flexible, and highly elastic. As a result of this function, injuries to the skin can occur. Wounds, which are caused by physical means, result in a disruption of the normal continuity of the structures of the skin. Examples of wounds include cuts, punctures, lacerations, etc.

Whereas skin is composed of an external covering of epithelium, the stomach lining is also composed of internal epithelium (endothelium). Gastric ulcers are a result of damage or erosion of the stomach lining. Gastric ulcers occur along the lesser curvature of the stomach where the pyloric glands border the oxyntic gland. They are usually 1 to 2.5 cm in diameter; however, they can vary from a few mm to several cm. Ulcers are usually round, oval or elliptical, with sharply defined margins. The surrounding mucosa is often hyperemic and edematous. Ulcers penetrate into the submucosa or muscular layer. A thin layer of gray or white exudate usually covers the base of the ulcers; this layer is composed of fibrinoid, granulation and fibrous tissue layers. During healing, fibrous tissue in the base contracts the ulcer and may distort the surrounding tissue. Healing continues as granulation tissue fills the base and epithelium from the ulcer edges cover its surface.

Healing usually requires two to six weeks but may require a longer time, especially if the ulcer is large or of a longstanding nature. If complete healing of the ulcer does not occur (as monitored by X-ray or endoscopic exam), surgery is usually considered in an effort to prevent complications or a prolonged, distressing course. *The Merck Manual of Diagnosis and Therapy*, 14th ed., by Merck Sharp & Dohme Research Laboratories (1982).

The mechanism of epithelial wound healing is a complex process involving ultrastructural changes of epithelial cells. These changes allow for detachment from neighboring cells, migration and subsequent reattachment. The migration of epithelial cells has been found to depend on a suitable matrix composed of fibrin, fibronectin or basement membrane which traverse the wound. Clark, R., *J. Am. Acid Derm.*, 13:701-718 (1985); Zitelli, J., *Adv. Dermatol.* 2:243-268 (1987).

There are two types of healing processes: (1) primary union or first intention healing and (2) secondary union or second intention healing. Primary union occurs when a clean wound with a minimal loss of tissue heals together cleanly. The process involves clotting and formation of a crust or scab to seal the wound; an acute inflammatory reaction; reepithelialization of the surface and fibrous bridging due to fibrin followed by complete sealing of the wound by an epithelial covering. Thereafter, hair follicles, sebaceous glands and sweat glands may subsequently regenerate. The process of second intention healing requires the removal of necrotic debris. The gap in the wound then fills in with fibrous materials.

When dealing with gastric ulcers the major objectives of therapy are relief of pain and healing of the ulcer. In a number of countries (not the U.S.) carbenoxolene is used to treat gastric ulcers. Carbenoxolene is a hydrolytic product of glycyrrhizic acid (derivative of licorice); it has been shown to increase the rate of gastric ulcer healing. Braunwald, E., *Harrison's Principles of Internal Medicine* 11th ed. p. 1247. It appears to increase the life span of gastric mucosal epithelial cells and increase the secretion and viscosity of gastric mucus. However, carbenoxolene has aldosterone-like effects, therefore it tends to increase the rate at which the body retains sodium and water. These effects may be blocked by aldosterone-antagonists, however the antagonists obliterate the healing effects of the carbenoxolene. There is a need for therapies which can promote healing without the negative side effects.

It has recently become clear that the skin may be a target tissue for 1,25—$(OH)_2$-$D_3$ (Stumpf, W. E. et al., *Science*, 206:1188-1190 (1979)). Cells isolated from the skin of rats, mice, and humans, and from cultured human skin fibroblasts and keratinocytes contain a high affinity ($1.0 \times 10^{-10}$ M) low capacity receptor-like protein for 1,25-dihydroxyvitamin $D_3$ (Franceschi, et al., *Arch. Biochem. Bioshys.*, 210: 1-13 (1979); Simpson, R. U. et al., *P.N.A.S. (USA)*, 77: 5822 (1980); Colston, K. et al., *Endocrinology*, 107: 1916 (1980); Feldman, D. et al., *Journal of Clinical Endocrinology & Metabolism*, 51: 1463 (1980); Eil, C. et al., *P.N.A.S. (USA)*, 78: 2562 (1981); and Clemens, T. L. et al., *J. Clin. Endocr. Metab.* 56: April 1983)). A specific biological function for 1,25—$(OH)_2$-vitamin $D_3$ in the skin, however, has yet to be discovered. Nevertheless, evidence has come forth supporting the concept that the dihydroxy metabolite of the vitamin does have biologic actions in the skin. This evidence was obtained evaluating the biological activity of 1,25-dihydroxy vitamin $D_3$ simultaneously in cultured human skin fibroblasts that either possessed or lacked a cytosolic receptor-like protein for the hormone (Clemens, T. L. et al., *J. Clin Endocrinol. Metab.*, 56: April 1983). The receptor-negative skin fibroblasts were obtained from a patient with a rare bone disorder called vitamin D dependent rickets, type II, a heritable disorder caused by a defective or complete absence of a cytoplasmic or nuclear receptor for 1,25-dihydroxyvitamin D. Administration of the dihydroxy metabolite of vitamin $D_3$ caused a dose-dependent inhibition of cell growth in receptor positive skin fibroblasts (about 40-50% reduction in cell growth was observed in cultures containing $10^{-6}$ and $10^{-8}$ M of hormone and 12% in cultures containing $10^{-10}$ M of 1,25—(OH)₂-D₃), and, by contrast, had absolutely no effect on the growth of receptor negative skin fibroblasts.

Holick et al. (*New England Journal of Medicine*, 303:349-354 (1980)) have studied the feasibility of using the skin as an organ for the synthesis and absorption of vitamin D metabolites. These investigators demonstrated that topical application of various vitamin D metabolites or pro-vitamin forms followed by phototherapy results in elevated serum levels of dihydroxyvitamin $D_3$. It was therefore suggested that topical application of vitamin D analogues may be an effective method of therapy for diseases involving calcium, phosphorous and bone metabolism problems.

Holick, U.S. Pat. No. 4,410,515, discloses vitamin D glycosides and their use in the regulation of calcium metabolism and phosphorous homeostasis.

Holick, U.S. Pat. No. 4,521,410, discloses water-soluble glycosyl orthoesters of vitamin D and their use in the regulation of calcium metabolism and phosphorous homeostasis.

Holick, U.S. Pat. No. 4,335,120, discloses that the toxic effects of orally administered vitamin $D_2$ and vitamin $D_3$ compounds can be avoided by topical administration whereby a slow and controlled transportation of the vitamin D compounds into the blood stream of a subject is achieved.

Jackson, U.S. Pat. No. 3,655,881 (1972) discloses methods for treating burned skin by inducing a state of calciphylaxis. Calciphylaxis is a hypersensitivity reaction resulting from the administration of or endogenous production of a sensitizing calcifier in combination with a challenger. Sensitizing calcifiers include, inter alia, vitamins $D_2$ and $D_3$.

Dikstein, U.S. Pat. No. 4,610,478, and European Patent Application No. 0 129 003 (1984), discloses compositions containing 1-alpha-hydroxycholecalciferol or 1-alpha,25-dihydroxycholecalciferol for the topical treatment of skin disorders, such as dermatitis, psoriasis, eczema, solar keratosis and certain stages of wound healing and alopecia. Dikstein also teaches that low dosages are required, from about 0.03 μg to 1.0 μg per gram of composition, to minimize the risk of undesired side effects and systemic effects. However, Dikstein does not teach that vitamin D compounds are useful for the treatment of wounds caused by lacerations, punctures or cuts.

Additionally, no specific therapy is available for healing decubitus or diabetic ulcers of the feet, however it is suggested that a course of aggressive supportive treatment can lead to salvaging the limb. Therefore, a need exists for effective treatments for diabetic ulcers.

SUMMARY OF THE INVENTION

Despite the teaching of Dikstein high doses of 1-alpha-hydroxycholecalciferol or 1-alpha,25-dihydroxycholecalciferol must be avoided, the inventors have discovered that the topical administration of relatively high levels of active vitamin D compounds and homologues, analogues, and hydroxylated metabolites thereof are therapeutically useful, in particular, for the treatment of wounds, ulcers, and periodontal disease.

In particular, the invention relates to a method of enhancing the healing of wounds in a patient comprises administering to said patient an effective amount of a vitamin D compound, wherein said vitamin D compound has the Formula (I):

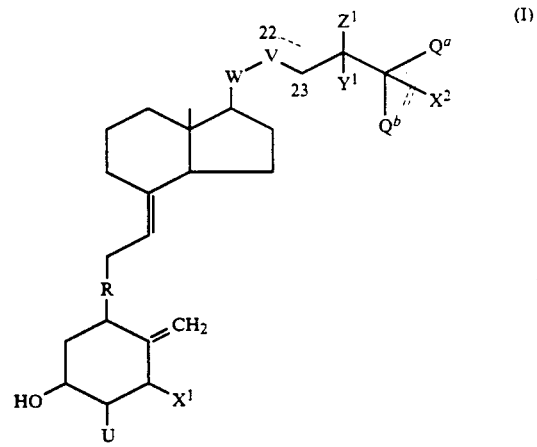

wherein the bond between carbons C-22 and C-23 is single or double bond;
$Y^1$ is hydrogen, F, $CH_3$, $CH_2CH_3$ or $X^1$;
U is hydrogen, —OH or —O—($C_2$–$C_4$ alkyl)—OH;
$Z^1$ is F, H or $X^1$;
$Q^a$ is $CF_3$ or $CH_2X^1$;
$Q^b$ is $CF_3$ or $CH_3$;
R is a double bond or an epoxy group;
wherein $X^1$ is selected from the group consisting of hydrogen and —OH;
W is CH—$CH_3$ or O; and
V is $CH_2$ or O;
with the proviso that both W and V are not both O; and
"= = =" is either a single bond between $Q^a$ and $Q^b$ or a hydrogen atom on $Q^a$ and $Q^b$, with the proviso that wherein "= = =" is a single bond, then $X^1$ is H.

The invention also relates to a method of enhancing the healing of wounds in a patient which comprises administering to said patient an effective amount of a vitamin D compound, wherein said vitamin D compound has the Formula (II):

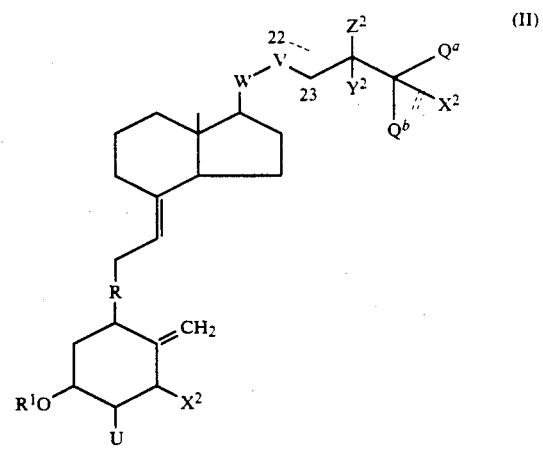

wherein the bond between C-22 and C-23 is a single or double bond;
$Y^2$ is hydrogen, fluorine, methyl, ethyl or $OR^1$;
$Z^2$ is F, H or $X^2$;
U is hydrogen, —OH or —O—($C_2$–$C_4$ alkyl)—OH;
$Q^a$ is $CF_3$ or $CH_2 X^2$;

$Q^b$ is $CF_3$ or $CH_3$;

R is a double bond or an epoxy group;

$X^2$ is selected from the group consisting of hydrogen, and $OR^1$, $R^1$ is hydrogen or a straight or branched chain glycosidic residue containing 1-20 glycosidic units per residue, or $R^1$ is an orthoester glycoside moiety of the Formula (III):

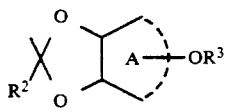
(III)

wherein A represents a glucofuranosyl or glucopyranosyl ring;

$R^2$ is hydrogen, lower alkyl, aralkyl, or aryl, with the proviso that aryl is phenyl or phenyl substituted by chloro, fluoro, bromo, iodo, lower $C_1$-$C_4$ alkyl, $C_1$-$C_4$ alkoxy; or naphthyl; and $R^3$ is hydrogen or a straight or branched chain glycosidic residue containing 1-20 glycosidic units per residue, with the proviso that at least one of the $R^1$ is either a glycosidic residue or an orthoester glycoside moiety;

W is CH—$CH_3$ or O; and

V is $CH_2$ or O;

with the proviso that both W and V are not both O; and

"= = =" is either a single bond between $Q^a$ and $Q^b$ or a hydrogen atom on $Q^a$ and $Q^b$, with the proviso that wherein "= = =" is a single bond, then $X^1$ is H.

The invention also relates to a method of inhibiting scar formation in a patient arising from cuts, lacerations, puncture wounds and abrasions which comprises administering to said patient a pharmaceutical composition comprising an effective amount of a vitamin D compound and a pharmaceutically acceptable carrier, wherein said vitamin D compound has the Formula (I):

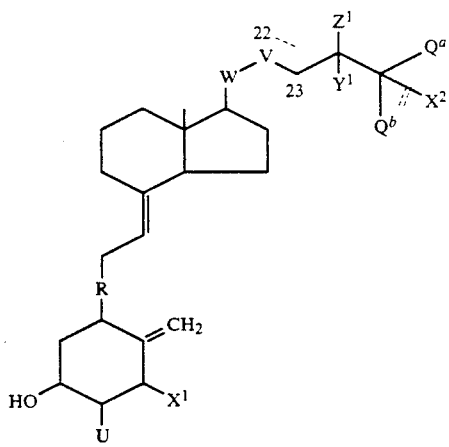
(I)

wherein the bond between carbons C-22 and C-23 is single or double bond;

$Y^1$ is hydrogen, F, $CH_3$, $CH_2CH_3$ or $X^1$;

U is hydrogen, —OH or -O-($C_2$-$C_4$ alkyl)—OH;

$Z^1$ is F, H or $X^1$;

$Q^a$ is $CF_3$ or $CH_2X^1$;

$Q^b$ is $CF_3$ or $CH_3$;

R is a double bond or an epoxy group;

wherein $X^1$ is selected from the group consisting of hydrogen and —OH;

W is CH—$CH_3$ or O; and

V is $CH_2$ or O;

with the proviso that both W and V are not both O; and

"= = =" is either a single bond between $Q^a$ and $Q^b$ or a hydrogen atom on $Q^a$ and $Q^b$, with the proviso that wherein "= = =" is a single bond, then $X^1$ is H.

The invention also relates to a method for inhibiting scar formation in a patient arising from cuts, lacerations, puncture wounds and abrasions which comprises topically administering to said patient a pharmaceutical composition comprising an effective amount of a vitamin D compound and a pharmaceutically acceptable carrier, wherein said vitamin D compound has the Formula (II):

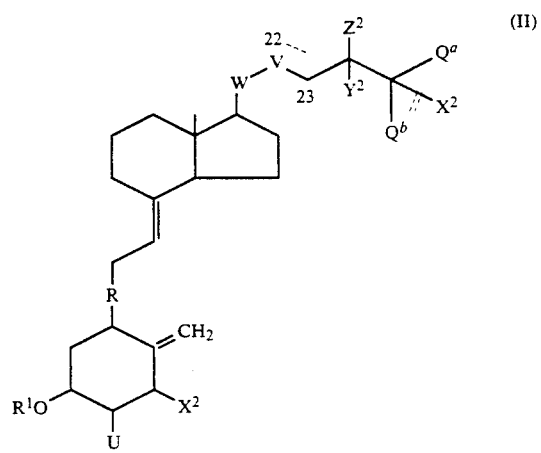
(II)

wherein the bond between C-22 and C-23 is a single or double bond;

$Y^2$ is hydrogen, fluorine, methyl, ethyl or $OR^1$;

U is hydrogen, —OH or —O—($C_2$-$C_4$ alkyl)—OH;

$Z^2$ is F, H or $X^2$;

$Q^a$ is $CF_3$ or $CH_2X^2$;

$Q^b$ is $CF_3$ or $CH_3$;

R is a double bond or an epoxy group;

$X^2$ is selected from the group consisting of hydrogen, and $OR^1$;

$R^1$ is hydrogen or a straight or branched chain glycosidic residue containing 1-20 glycosidic units per residue, or $R^1$ is an orthoester glycoside moiety of the Formula (III):

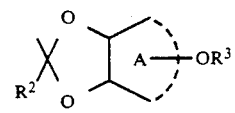
(III)

wherein A represents a glucofuranosyl or glucopyranosyl ring;

$R^2$ is hydrogen, lower alkyl, aralkyl, or aryl, with the proviso that aryl is phenyl or phenyl substituted by chloro, fluoro, bromo, iodo, lower $C_1$-$C_4$ alkyl, $C_1$-$C_4$ alkoxy; or naphthyl; and $R^3$ is hydrogen or a straight or branched chain glycosidic residue containing 1-20 glycosidic units per residue;

W is CH—CH$_3$ or O; and

V is CH$_2$ or O;

with the proviso that both W and V are not both O; and

"= = =" is either a single bond between Q$^a$ and Q$^b$ or a hydrogen atom on Q$^a$ and Q$^b$, with the proviso that wherein "= = =" is a single bond, then X$^1$ is H.

The invention also relates to a method of treating gastric, duodenal, esophageal, decubitus, diabetic foot and genito-urinary ulcers in a patient which comprises administering to said patient a pharmaceutical composition comprising an effective amount of a vitamin D compound and a pharmaceutically acceptable carrier, wherein said vitamin D compound has the Formula (I):

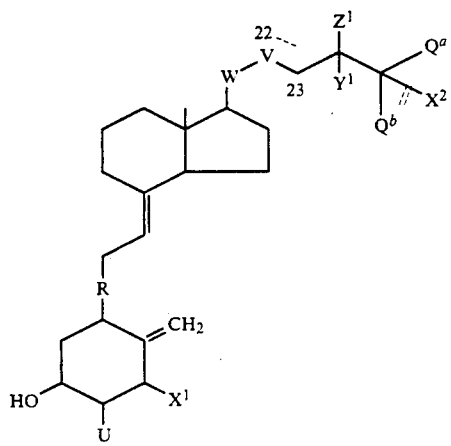

(I)

wherein the bond between carbons C-22 and C-23 is single or double bond;

Y$^1$ is hydrogen, F, CH$_3$, CH$_2$CH$_3$ or X$^1$;

U is hydrogen, —OH or —O—(C$_2$-C$_4$ alkyl)—OH;

Z$^1$ is F, H or X$^1$;

Q$^a$ is CF$_3$ or CH$_2$X$^1$;

Q$^b$ is CF$_3$ or CH$_3$;

R is a double bond or an epoxy group;

wherein X$^1$ is selected from the group consisting of hydrogen and —OH;

W is CH—CH$_3$ or O; and

V is CH$_2$ or O;

with the proviso that both W and V are not both O; and

"= = =" is either a single bond between Q$^a$ and Q$^b$ or a hydrogen atom on Q$^a$ and Q$^b$, with the proviso that wherein "= = =" is a single bond, then X$^1$ is H.

The invention also relates to a method for treating gastric, duodenal, esophageal, decubitus, diabetic foot, genito-urinary ulcers and ulcerative keratitis in a patient which comprises topically or ophthalmically administering to said patient a pharmaceutical composition comprising an effective amount of a vitamin D compound and a pharmaceutically acceptable carrier, wherein said vitamin D compound has the Formula (II):

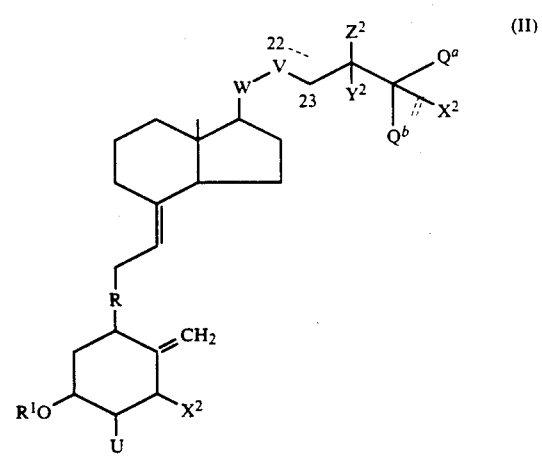

(II)

wherein the bond between C-22 and C-23 is a single or double bond;

Y$^2$ is hydrogen, fluorine, methyl, ethyl or OR$^1$;

U is hydrogen, —OH or —O—(C$_2$-C$_4$ alkyl)—OH;

Z$^2$ is F, H or X$^2$;

Q$^a$ is CF$_3$ or CH$_2$X$^2$;

Q$^b$ is CF$_3$ or CH$_3$;

R is a double bond or an epoxy group;

X$^2$ is selected from the group consisting of hydrogen, and OR$^1$;

R$^1$ is hydrogen or a straight or branched chain glycosidic residue containing 1-20 glycosidic units per residue, or R$^1$ is an orthoester glycoside moiety of the Formula (III):

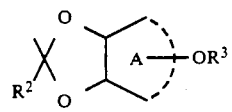

(III)

wherein A represents a glucofuranosyl or glucopyranosyl ring;

R$^2$ is hydrogen, lower alkyl, aralkyl, or aryl, with the proviso that aryl is phenyl or phenyl substituted by chloro, fluoro, bromo, iodo, lower C$_1$-C$_4$ alkyl, C$_1$-C$_4$ alkoxy; or naphthyl; and R$^1$ is hydrogen or a straight or branched chain glycosidic residue containing 1-20 glycosidic units per residue;

W is CH—CH$_3$ or O; and

V is CH$_2$ or O; with the proviso that both W and V are not both O; and

"= = =" is either a single bond between Q$^a$ and Q$^b$ or a hydrogen atom on Q$^a$ and Q$^b$, with the proviso that wherein "= = =" is a single bond, then X$^1$ is H.

DESCRIPTION OF THE PREFERRED EMBODIMENTS

Figure 1:
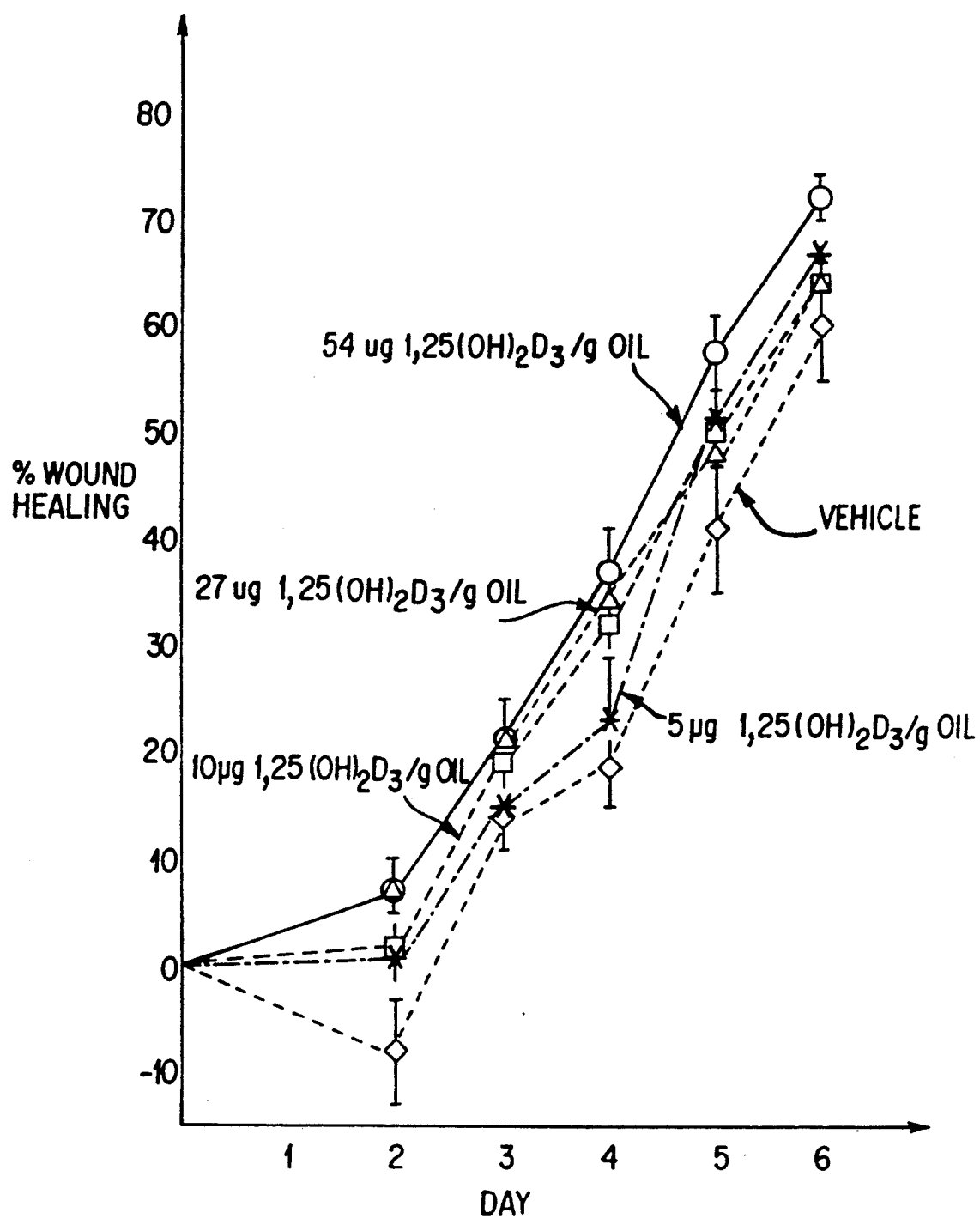
FIG. 1 depicts a graph showing the effect of vehicle and 5 μg, 10 μg, 27 μg and 54 μg of 1,25-dihydroxyvitamin D$_3$ per gram of oil on the percentage of wound healing on days 1, 2, 3, 4, 5 and 6 in rats with experimental wounds.

The present invention provides for a method of healing wounds and inhibiting scar formation. Wounds to the external epithelium include cuts, punctures and lacerations, including corneal lacerations. Wounds of the internal epithelium include peptic ulcers, esophageal mucosa injury, oral mucosa injuries and periodontal disease. The invention also provides for the treatment of ulcers such as diabetic ulcers of the feet, decubitus ulcers (bed sores), genito-urinary ulcers, peptic ulcers and ulcerative keratitis. Ulcerative keratitis is caused, for example, by extended wear of contact lenses.

As used herein, the term "septic ulcer" includes both duodenal and gastric ulcers. Peptic ulcers are a group of ulcerative disorders of the upper gastrointestinal tract; the primary forms of peptic ulcer are duodenal and gastric ulcer. Normally gastric mucosa has the ability to resist the corrosive effects of acid-pepsin. This is a trait which is unique to the gastric mucosa; areas such as the esophagus do not have this ability. Injury to the esophageal mucosa occurs from exposure to refluxed gastric juice and ulceration which occurs in the small intestine at the site of surgical attachment to actively secreting gastric mucosa.

Genito-urinary ulcers treatable with the vitamin D compounds of the invention include those caused by, for example, herpes simplex virus as well as other viral, fungal and bacterial infections. See Harrison's *Principles of Internal Medicine*, E. Braunwald et al. (eds.); McGraw-Hill Book Co., New York, N.Y., 1987, pp. 514–516.

The vitamin D compounds of the invention may also be administered for the treatment of periodontal disease. This disease begins as a marginal inflammation of the gingivae (gingivitis) which slowly spreads to involve the underlying alveolar bone and periodontal ligament. See Harrison's *Principals of Internal Medicine*, supra, pp. 164. The vitamin D compounds may be applied topically, for example, as part of a tooth paste formulation, or may be administered orally or part of a thin film implant between the teeth and gums to give sustained release of the vitamin D compound. Preferably, the film comprises a cellulose polymer. See U.S. Pat. No. 4,315,779 to Heyd.

Among the preferred compounds usable in the present invention are those of the formula (I):

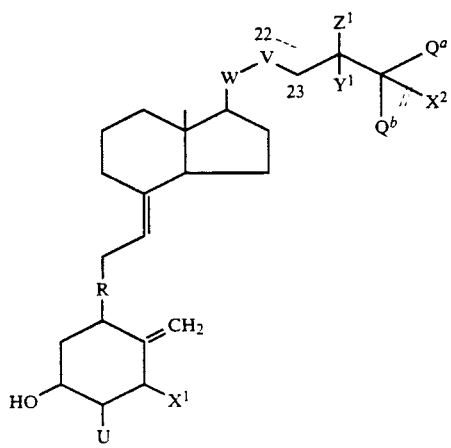

(I)

wherein the bond between carbons C-22 and C-23 is single or double;

$Y^1$ is hydrogen, F, $CH_3$, $CH_2CH_3$ or $X^1$;

U is hydrogen, —OH or —O—($C_2$–$C_4$ alkyl)—OH;

$Z^1$ is F, H or $X^1$;

$Q^a$ is $CF_3$ or $CH_2X^1$;

$Q^b$ is $CF_3$ or $CH_3$;

R is a double bond or an epoxy group;

$X^1$ and $X^2$ are selected from the group consisting of hydrogen and OH;

W is CH—$CH_3$ or O; and

V is $CH_2$ or O;

with the proviso that both W and V are not both O; and

"= = =" is either a single bond between $Q^a$ and $Q^b$ or a hydrogen atom on $Q^a$ and $Q^b$, with the proviso that wherein "= = =" is a single bond, then $X^1$ is H.

When the compounds of Formula (I) have a double bond at position C-22, they are derivatives of vitamin $D_2$, whereas if the bond at that position is single, and there is a lack of $C_{24}$ alkyl, they are derivatives of vitamin $D_3$. The latter are preferred.

Preferred are those compounds derived from vitamins $D_3$ or $D_2$; 1-hydroxyvitamins $D_3$ or $D_2$; 1,24-dihydroxyvitamins $D_2$ and $D_3$; 1,25-dihydroxyvitamins $D_3$ and $D_2$; 24,25-dihydroxyvitamins $D_3$ or $D_2$; 25,26-hydroxyvitamins $D_3$ or $D_2$; 1,24,25-trihydroxyvitamins $D_3$ or $D_2$. Most preferred among these are vitamins $D_3$ or $D_2$; 1-hydroxyvitamins $D_3$ or $D_2$; and 1,25-dihydroxyvitamins $D_3$ or $D_2$,5,6-epoxy derivatives of vitamin D and its metabolites, 2-β-(3-hydroxypropoxy)-1 alpha,25-dihydroxyvitamin $D_3$, as well as the side chain fluoro derivatives of 1,25-(OH)$_2$ vitamin D and 1-(OH) vitamin D. Also preferred are 20- and 22-oxa vitamin D derivatives including 20-oxa-1α(OH)D, 20-oxa-1α,2-5(OH)$_2$D$_3$, 22-oxa-1α(OH)D$_3$ and 22-oxa-1α,25(OH)D$_3$ as well as pseudo-1-alpha-hydroxyvitamin D derivatives such as dihydrotachysterol and 5,6-trans vitamin D$_3$ and their 25-hydroxy derivatives.

Among other preferred compounds are water soluble derivatives of the aforementioned compounds of Formula (I) obtained by solubilizing such compounds by attaching thereto glycosidic residues such as those disclosed in Holick, U.S. Pat. No. 4,410,515. Alternative methods of solubilization are by conjugating compounds of Formula (I) to glycosyl orthoester residues, as disclosed in copending U.S. Ser. No. 607,117 by Holick et al., filed May 3, 1984. The disclosures of the aforementioned patent and application are herein incorporated by reference and made a part hereof.

Also useful in the practice of the invention are compounds of the Formula (II):

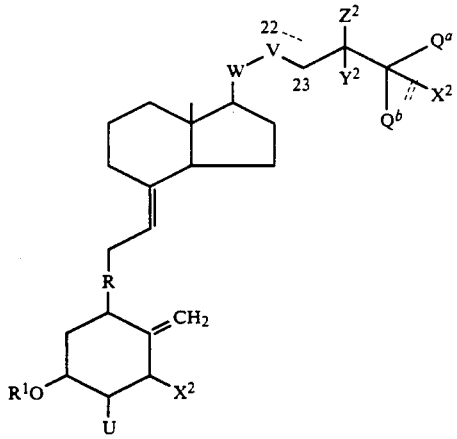

(II)

wherein $Y^2$ is hydrogen, fluorine, methyl, ethyl or $OR^1$;
$Z^2$ is F, H or $X^2$;
U is hydrogen, —OH or —O—($C_2$-$C_4$ alkyl)—OH;
$Q^a$ and $Q^b$ have the same meanings as in Formula (I);
R is a double bond or an epoxy group;
$X^2$ is selected from the group consisting of hydrogen and $OR^1$;
$R^1$ is hydrogen or a straight or branched chain glycosidic residue containing 1-20 glycosidic units per residue, or $R^1$ is an orthoester glycoside moiety of the Formula (III):

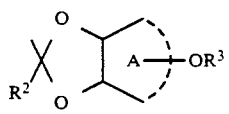

(II)

wherein A represents a glucofuranosyl or glucopyranosyl ring;
$R^2$ is hydrogen, lower alkyl ($C_1$-$C_4$), aralkyl ($C_7$-$C_{10}$), or aryl, with the proviso that aryl is phenyl or phenyl substituted by chloro, fluoro, bromo, iodo, lower $C_1$-$C_4$ alkyl, $C_1$-$C_4$ alkoxy; or naphthyl;
$R^3$ is hydrogen or a straight or branched chain glycosidic residue containing 1-20 glycosidic units per residue;
W is CH—$CH_3$ or O; and
V is $CH_2$ or O; with the proviso that both W and V are not both O; and
"= = =" is either a single bond between $Q^a$ and $Q^b$ or a hydrogen atom on $Q^1$ and $Q^b$, with the proviso that wherein "= = =" is a single bond, then $X^2$ is H; and
with the further proviso that at least one of the $R^1$ is either a glycosidic residue or an orthoester glycoside moiety.

The vitamin D compounds are prepared or obtained according to the disclosures of the aforementioned references. In particular, the 5,6-epoxy derivatives of vitamin $D_3$ are obtained as described in *Jpn. Kokai Tokkyo Koho* JP 58,216,178 [83,216,178], Dec. 15, 1983. The fluoro derivatives are made or obtained as described in Shiina, et al., *Arch. Biochem. Biophys* 220:90 (1983). Methods for preparing the 20- and 22-oxa vitamin D derivatives are disclosed by Abe, J., et al., *Vitamin D Molecular, Cellular and Clinical Endocrinology* 310-319, Walter de Gruyter & Co., Berlin (1988). U.S. Pat. No. 4,719,205 to DeLuca et al. discloses methods for the preparation of 22,23-cis-unsaturated, 1-hydroxyvitamin D compounds. U.S. Pat. No. 4,634,692 to Partridge et al. discloses methods for the preparation of 1,25-dihydroxy-24 (R or S)-fluorovitamin D. Japanese Patent Application, publication No. J55 111-460, discloses methods for the preparation of 24,24-difluoro-25-hydroxyvitamin $D_3$.

The compounds of the invention can be administered in any appropriate pharmaceutically acceptable carrier for oral, parenteral, or topical administration. They can be administered by any means that enhances wound healing, ulcer healing, amelioration of periodontal disease, and inhibition of scar formation in animals, especially humans. The dosage administered will be dependent upon the age, health and weight of the recipient, kind of concurrent treatment, if any, frequency of treatment and the nature of the effect desired. For example, systemic daily dosage of 1,25-dihydroxyvitamin $D_3$ will be from about 0.001 micrograms/kg to 100 micrograms/kg preferably 0.01 to 1.0 micrograms per kg of body weight. Normally, from 0.1 to 100 micrograms/kg per day of 1,25-dihydroxyvitamin $D_3$, in one or more dosages per day is effective to obtain the desired results. Dosage forms for topical administration include about 3 to 100 micrograms of 1,25-dihydroxyvitamin $D_3$ per gram of carrier. Preferably, the dosage form contains about 5 $\mu$g to 3 mg of 1,25-dihydroxyvitamin $D_3$ per gram of carrier. More preferably, the dosage form contains about 10 to 30 micrograms of 1,25-dihydroxyvitamin $D_3$ per gram of carrier. A most preferred dosage form contains about 15 ug of 1,25-dihydroxyvitamin $D_3$ per gram of carrier. One of ordinary skill in the art can determine the optimal dosages and concentrations of other active vitamin D compounds with only routine experimentation.

The compounds can be employed in dosage forms such as tablets, capsules, powder packets, or liquid solutions, suspensions or elixirs for oral administration, sterile liquid for formulations such as solutions or suspensions for parenteral use. Alternatively, the compounds can be present in a pharmacologically inert topical carrier such as one comprising a gel, an ointment or a cream, including such carriers as water, glycerol, alcohol, propylene glycol, fatty alcohols, triglycerides, fatty acid esters or mineral oils. Other possible carriers are liquid petroleum, isopropylpalmitate, polyethylene glycol ethanol 95%, polyoxyethylene monolaurate 5% in water, sodium lauryl sulfate 5% in water, and the like. Materials such as anti-oxidants, humectants, viscosity stabilizers and the like may be added, if necessary. The compounds may also be present as part of a cosmetic formulation which may be formulated according to methods known to those of skill in the art. The compounds can also be administered by means of pumps, tapes or patches.

Having now generally described this invention, the same will be understood by reference to the following examples which are provided herein for purposes of illustration only and are not intended to be limiting unless otherwise specified.

EXAMPLES

Example 1 The Effects of 1,25(OH)$_2$D$_3$ on Wound Healing in Rats

Materials

25 CD rats 8 weeks old were obtained from Charles River Laboratories, Inc., Wilmington, Ma.

Wounding Procedure

Rats were anesthetized with ether. Their backs were prepared by clipping and shaving. Two cutaneous wounds were made on each rat by punching on the right and left sides of the back with a sterile biopsy punch (diameter 4mm, wound thickness: full thickness of skin).

Control rats received vehicle only on wounds (20 μl vegetable oil/two wounds/day for 4 days). The other four groups of rats (5 rats per group) were used to study the effect of 1,25(OH)$_2$D$_3$ on wound healing at different doses (5 μg 1,25(OH)$_2$D$_3$/g Oil, 10 μg/g oil, 27 μg/g oil and 54 μg/g oil 1,25 (OH)$_2$D$_3$). Treatment continued for up to 4 days.

Measurement Procedure

Wound area was estimated by planimetry. For this purpose, the wound was covered with a transparent plastic film and wound outlines were drawn with a marker. Wound shape was then magnified, was cut out, and weighed.

Healing was assessed as the decrease in wound area on days 2, 3, 4, 5 and 6. The results are shown in Table I below and is depicted in FIG. 1. The data (percent healing on day 2, 3, 4, 5 and 6) were analyzed for significance using students T test.

In order to confirm the effectiveness of 1,25-(OH)$_2$D$_3$ in promoting wound healing, a second experiment was carried out using eight rats (dose of 1,25(OH)$_2$D$_3$=27 μg/g oil). The results are depicted in FIG. 2.

Results

Figure 2:
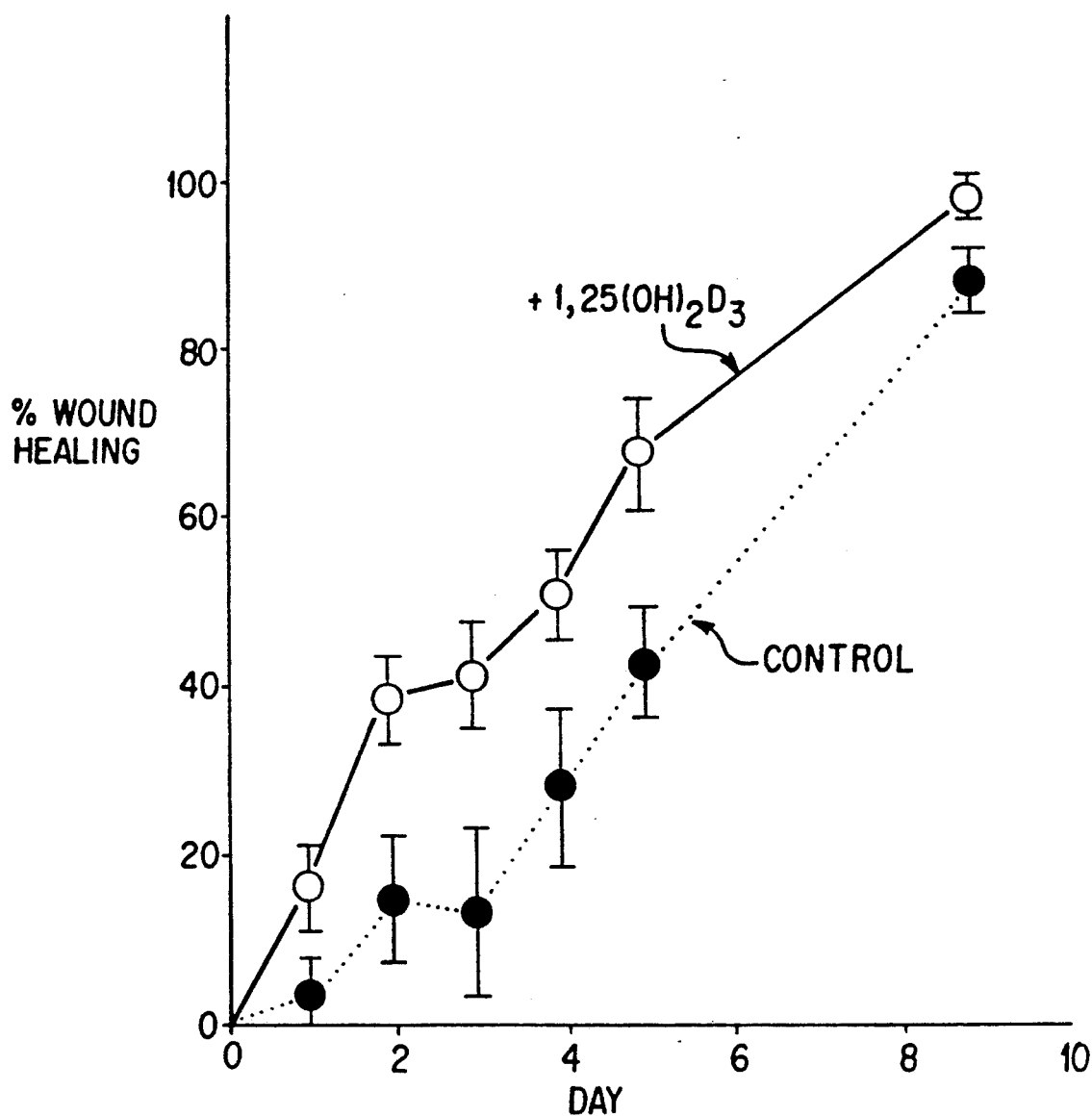
FIG. 2 depicts a graph showing the effect of vehicle and 27 μg 1,25-dihydroxyvitamin D$_3$/gram oil on the percentage of wound healing on days 1, 2, 3, 4, 5 and 9 in rats with experimental wounds.

As can be seen clearly in FIGS. 1 and 2, topical administration of 1,25(OH)$_2$D$_3$ enhanced substantially the healing of puncture wounds in rats. The extent of wound healing was directly related to the concentration of 1,25(OH)$_2$D$_3$ in oil applied to the wound. These results demonstrate conclusively that vitamin D compounds are useful for enhancing wound healing in individuals.

TABLE 1
EFFECT OF 1,25(OH)$_2$D$_3$ ON WOUND HEALING OF RATS

| GROUP | % HEALING[a] | | | | |
|---|---|---|---|---|---|
| | DAY 2 | DAY 3 | DAY 4 | DAY 5 | DAY 6 |
| 1. CONTROL | −8 ± 5[b] | 14 ± 3 | 19 ± 4 | 41 ± 6 | 60 ± 5 |
| 2. 1,25 (OH)$_2$D$_3$ (5 μg/g oil) | 1 ± 5 | 14 ± 7 | 23 ± 6 | 52 ± 5 | 67 ± 5 |
| 3. 1,25 (OH)$_2$D$_3$ (10 μg/g oil) | 2 ± 4 | 19 ± 4 | 32 ± 3§ | 50 ± 3 | 64 ± 3 |
| 4. 1,25 (OH)$_2$D$_3$ (27 μg/g oil) | 7 ± 4§ | 21 ± 3 | 34 ± 5§ | 48 ± 4 | 64 ± 4 |
| 5. 1,25 (OH)$_2$D$_3$ (54 μg/g oil) | 7 ± 4§ | 21 ± 4 | 37 ± 4# | 57 ± 4§ | 72 ± 2* |

[a]% HEALING = $\frac{\text{Original Wound Area} - \text{Lesion Area}}{\text{Original Wound Area}} \times 100\%$

[b]MEANS ± SEM, n-10

Significance of difference from control using Student's t test: * p < .05, § p < .025 and # p < .005

What is claimed as new and desired to be covered by U.S. Letters Patent is:

1. A method of treating periodontal disease in an animal which comprises administering to said animal a pharmaceutical composition comprising a therapeutically effective amount of a vitamin D compound and a pharmaceutically acceptable carrier, wherein said vitamin D compound has the formula:

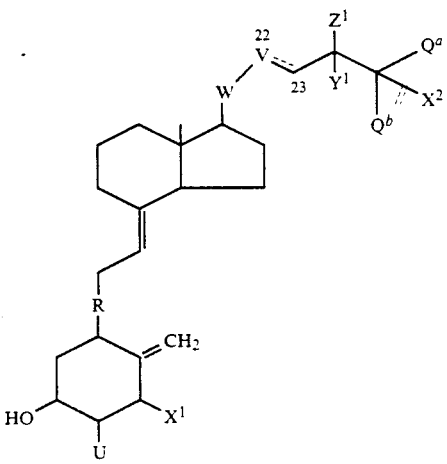

wherein the bond between carbons C-22 and C-23 is single or double bond;

Y$^1$ is hydrogen, F, CH$_3$, CH$_2$CH$_3$ or X$^1$;

U is hydrogen, —OH or —O—(C$_2$-C$_4$ alkyl)—OH;

Z$^1$ is F, H or X$^1$;

Q$^a$ is CF$_3$ or CH$_2$X$^1$;

Q$^b$ is CF$_3$ or CH$_3$;

R is a double bond or an epoxy group;

wherein X$^1$ and X$^2$ are selected form the group consisting of hydrogen and —OH;

W is CH—CH$_3$ or O; and

V is CH$_2$ or O; with the proviso that both W and V are not both O; and

"= = =" is either a single bond between Q$^a$ and Q$^b$ or a hydrogen atom on Q$^1$ and Q$^b$, with the proviso that wherein "= = =" is a single bond, then X$^2$ is H.

2. The method of claim 1, wherein said bond between carbons C-22 and C-23 is a single bond and X$^1$ is hydrogen.

3. The method of claim 1, wherein said bond between C-22 and C-23 is a single bond, X$^1$ is hydroxyl, and at least one of the group consisting of Y$^1$, Z$^1$, Q$^a$ and Q$^b$ contains a fluorine atom.

4. The method of claim 1, wherein said bond between C-22 and C-23 is a double bond.

5. The method of claim 1, wherein said bond between C-22 and C-23 is a double bond and X$^1$ is hydrogen.

6. The method of claim 1, wherein said bond between C-22 and C-23 is a double bond and $X^1$ is hydroxyl.

7. A method of treating periodontal disease in an animal which comprises administering to said animal a pharmaceutical composition comprising a effective amount of a vitamin D compound and a pharmaceutically acceptable carrier, wherein said vitamin D compound has the formula:

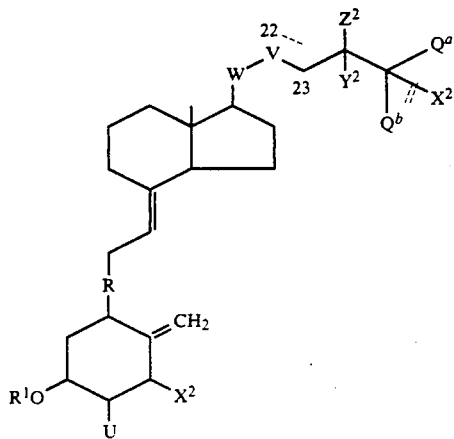

wherein the bond between carbons C-22 and C-23 is single or double bond;
$Y^2$ is hydrogen, fluorine, methyl, ethyl or $OR^1$;
U is hydrogen, —OH or —O—$(C_2$-$C_4$ alkyl)—OH;
$Z^2$ is F, H or $X^2$;
$Q^a$ is $CF_3$ or $CH_2X^2$;
$Q^b$ is $CF_3$ or $CH_3$;
R is a double bond or an epoxy group;
$X^2$ is selected form the group consisting of hydrogen and —$OR^1$;
wherein R1 is hydrogen or a straight or branched chain glycosidic residue containing 1–20 glycosidic units per residue, or $R^1$ is an orthoester glycoside moiety of the formula:

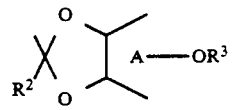

wherein A represents a glucofuranosyl or glucopyranosyl ring;
$R^2$ is hydrogen, lower alkyl, aralkyl, or aryl, with the proviso that aryl is phenyl or phenyl substituted by chloro, fluoro, bromo, iodo, lower $C_1$-$C_4$ alkyl, $C_1$-$C_4$; or naphthyl; and
$R^3$ is hydrogen or a straight or branched chain glycosidic residue containing 1–20 glycosidic units per residue, with the proviso that said vitamin D compound has at least one $R^1$ which is a glycosidic residue or an orthoester glycoside moiety;
W is CH—$CH_3$ or O; and
V is $CH_2$ or O; with the proviso that both W and V are not both O; and
"= = =" is either a single bond between $Q^1$ and $Q^b$ or a hydrogen atom on $Q^a$ and $Q^b$, with the proviso that wherein "= = =" is a single bond, then $X^2$ at C-25 is H.

8. The method of claim 7, wherein said bond between C-22 and C-23 is a single bond and at least one of the group consisting of $Y^1$, $Z^1$, $Q^a$ and $Q^b$ contains a fluorine atom.

* * * * *